(12) United States Patent
Wardle

(10) Patent No.: US 7,731,705 B2
(45) Date of Patent: Jun. 8, 2010

(54) ELUTING COILS AND METHODS OF DEPLOYING AND RETRIEVING

(76) Inventor: John L. Wardle, 1802 Arriba Linda, San Clemente, CA (US) 92672

( * ) Notice: Subject to any disclaimer, the term of this patent is extended or adjusted under 35 U.S.C. 154(b) by 1126 days.

(21) Appl. No.: 11/328,884

(22) Filed: Jan. 9, 2006

(65) Prior Publication Data

US 2006/0151460 A1 Jul. 13, 2006

Related U.S. Application Data

(60) Provisional application No. 60/642,892, filed on Jan. 10, 2005.

(51) Int. Cl.
*A61M 25/00* (2006.01)
(52) U.S. Cl. .................................... 604/523
(58) Field of Classification Search ................. 604/523
See application file for complete search history.

(56) References Cited

U.S. PATENT DOCUMENTS

| | | |
|---|---|---|
| 4,548,202 A | 10/1985 | Duncan |
| 4,616,656 A | 10/1986 | Nicholson et al. |
| 4,632,100 A | 12/1986 | Somers et al. |
| 4,774,948 A | 10/1988 | Markham |
| 4,843,651 A | 7/1989 | Gramaza |
| 4,883,070 A | 11/1989 | Hanson |
| 4,899,744 A | 2/1990 | Fujitsuka et al. |
| 4,924,865 A | 5/1990 | Bays et al. |
| 4,931,059 A | 6/1990 | Markham |
| 4,938,760 A | 7/1990 | Burton et al. |
| 5,002,548 A | 3/1991 | Campbell et al. |
| 5,007,921 A | 4/1991 | Brown |
| 5,013,316 A | 5/1991 | Goble et al. |
| 5,018,530 A | 5/1991 | Rank et al. |
| 5,104,399 A | 4/1992 | Lazarus |
| 5,123,906 A | 6/1992 | Kelman |
| 5,127,916 A | 7/1992 | Spencer et al. |
| 5,129,906 A | 7/1992 | Ross et al. |
| 5,141,520 A | 8/1992 | Goble et al. |
| 5,179,962 A | 1/1993 | Ducher et al. |
| 5,186,922 A | 2/1993 | Shell et al. |
| 5,219,358 A | 6/1993 | Bendel et al. |
| 5,221,269 A | 6/1993 | Miller et al. |
| 5,231,989 A | 8/1993 | Middleman et al. |
| 5,486,183 A | 1/1996 | Middleman et al. |
| 5,486,187 A | 1/1996 | Schenk |
| 5,489,295 A | 2/1996 | Piplani et al. |

(Continued)

OTHER PUBLICATIONS

Office Action mailed on:Jan. 25, 2008 in U.S. Appl. No. 10/386,260, filed Mar. 10, 2003 and published as: US-2006-0151460 on: Jul. 13, 2006.

(Continued)

*Primary Examiner*—Nicholas D Lucchesi
*Assistant Examiner*—Diva Ranade
(74) *Attorney, Agent, or Firm*—Grant Anderson LLP

(57) ABSTRACT

Embodiments are directed to eluting coils having a relaxed coiled state and a straightened state that may be deployed at a fixed location within a patient's body and may accurately dispense and distribute fluids and or dissolvable substances at site specific locations of the body. Some embodiments of eluting elements are configured to be subsequently retrieved from a delivery site.

19 Claims, 8 Drawing Sheets

U.S. PATENT DOCUMENTS

| | | | |
|---|---|---|---|
| 5,522,820 A | 6/1996 | Caspari et al. | |
| 5,527,323 A | 6/1996 | Jervis et al. | |
| 5,556,410 A | 9/1996 | Mittermeir et al. | |
| 5,571,117 A | 11/1996 | Ahn | |
| 5,571,285 A | 11/1996 | Chow et al. | |
| 5,573,543 A | 11/1996 | Akopov et al. | |
| 5,597,378 A | 1/1997 | Jervis | |
| 5,601,572 A * | 2/1997 | Middleman et al. | 606/139 |
| 5,628,783 A | 5/1997 | Quiachon et al. | |
| 5,645,567 A | 7/1997 | Crainich | |
| 5,662,683 A | 9/1997 | Kay | |
| 5,693,083 A | 12/1997 | Baker et al. | |
| 5,738,474 A | 4/1998 | Blewett | |
| 5,810,851 A | 9/1998 | Yoon | |
| 5,816,258 A | 10/1998 | Jervis | |
| 5,853,366 A | 12/1998 | Dowlatshahi | |
| 5,902,310 A | 5/1999 | Foerster et al. | |
| 6,042,607 A | 3/2000 | Williamson, IV et al. | |
| 6,165,183 A | 12/2000 | Kuehn et al. | |
| 6,168,598 B1 | 1/2001 | Martello | |
| 6,171,338 B1 | 1/2001 | Talja et al. | |
| 6,188,932 B1 | 2/2001 | Lindergren | |
| 6,220,248 B1 | 4/2001 | Voegele et al. | |
| 6,228,055 B1 | 5/2001 | Foerster et al. | |
| 6,234,177 B1 | 5/2001 | Barsch | |
| 6,235,051 B1 | 5/2001 | Murphy | |
| 6,256,543 B1 | 7/2001 | Spence | |
| 6,261,243 B1 | 7/2001 | Burney et al. | |
| 6,261,302 B1 | 7/2001 | Voegele et al. | |
| 6,270,464 B1 | 8/2001 | Fulton, III et al. | |
| 6,287,339 B1 | 9/2001 | Vazques et al. | |
| 6,312,429 B1 | 11/2001 | Burbank et al. | |
| 6,312,447 B1 | 11/2001 | Grimes | |
| 6,325,816 B1 | 12/2001 | Fulton, III et al. | |
| 6,332,864 B1 | 12/2001 | Schweich, Jr. et al. | |
| 6,332,893 B1 | 12/2001 | Mortier et al. | |
| 6,413,274 B1 | 7/2002 | Pedros | |
| 6,432,064 B1 | 8/2002 | Hibner et al. | |
| 6,447,523 B1 | 9/2002 | Middleman et al. | |
| 6,508,829 B1 | 1/2003 | Levinson et al. | |
| 6,514,263 B1 | 2/2003 | Stefanchik et al. | |
| 6,520,974 B2 | 2/2003 | Tanner et al. | |
| 6,520,980 B1 | 2/2003 | Foerster | |
| 6,752,154 B2 * | 6/2004 | Fogarty et al. | 128/899 |
| 6,766,186 B1 | 7/2004 | Hoyns et al. | |
| 2003/0225420 A1 * | 12/2003 | Wardle | 606/151 |
| 2004/0034357 A1 | 2/2004 | Beane et al. | |
| 2004/0193151 A1 * | 9/2004 | To et al. | 606/41 |
| 2008/0195146 A1 | 8/2008 | Wardle | |

OTHER PUBLICATIONS

Office Action mailed on:Sep. 26, 2007 in U.S. Appl. No. 10/386,260, filed Mar. 10, 2003 and published as: US-2006-0151460 on: Jul. 13, 2006.

Office Action mailed on:May 8, 2007 in U.S. Appl. No. 10/386,260, filed Mar. 10, 2003 and published as: US-2006-0151460 on: Jul. 13, 2006.

Office Action mailed on:Apr. 17, 2006 in U.S. Appl. No. 10/386,260, filed Mar. 10, 2003 and published as: US-2006-0151460 on: Jul. 13, 2006.

* cited by examiner

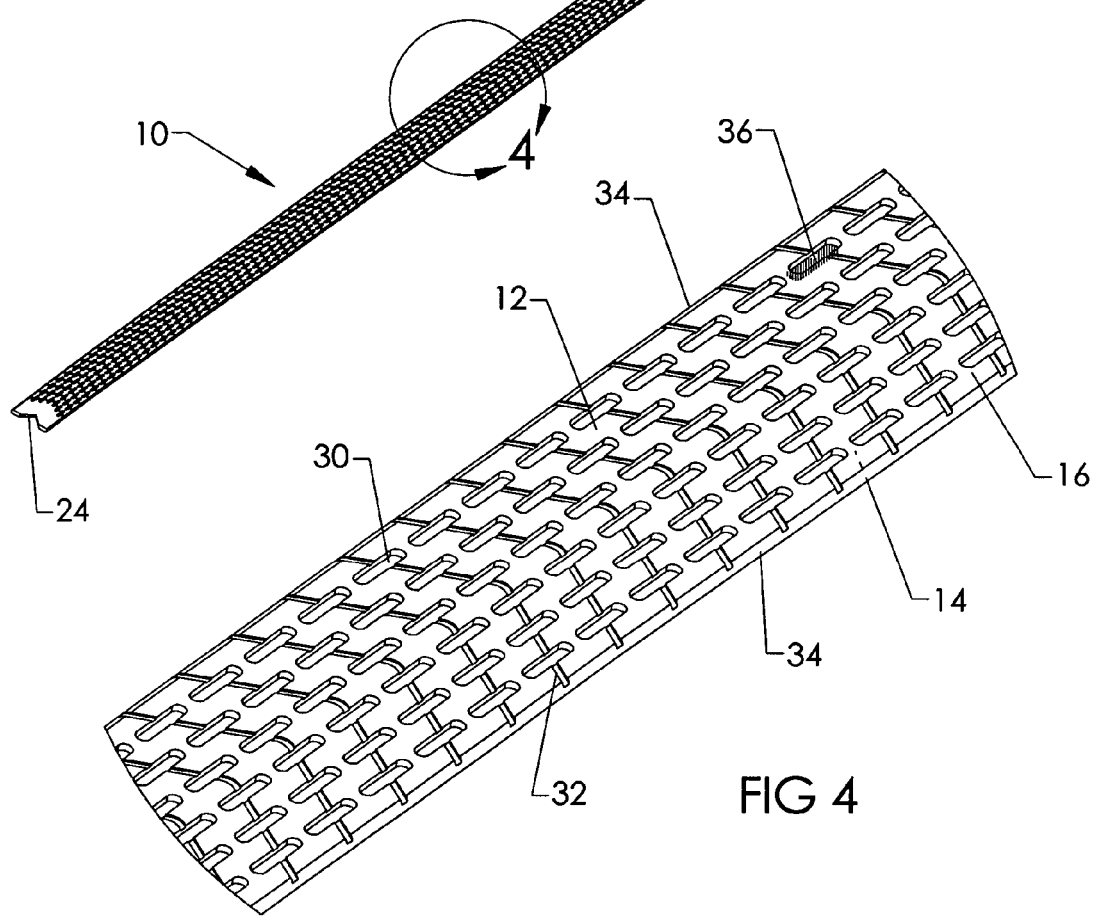

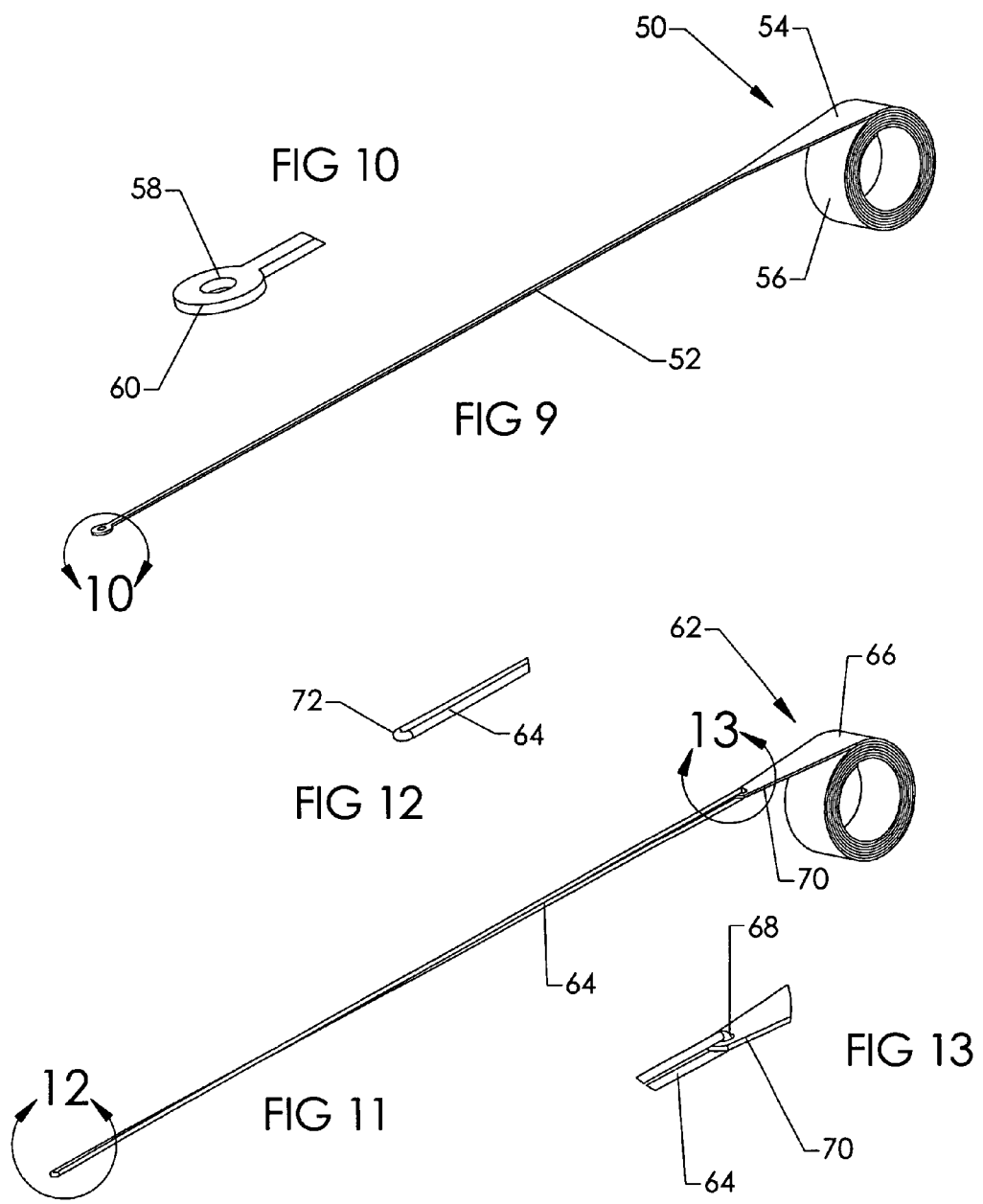

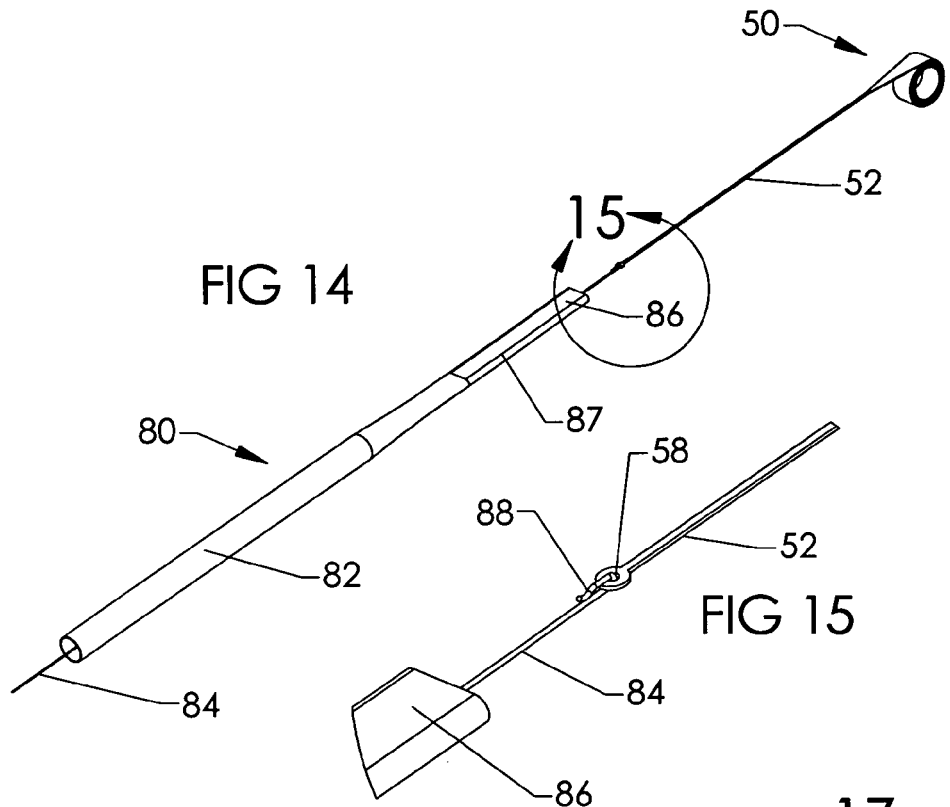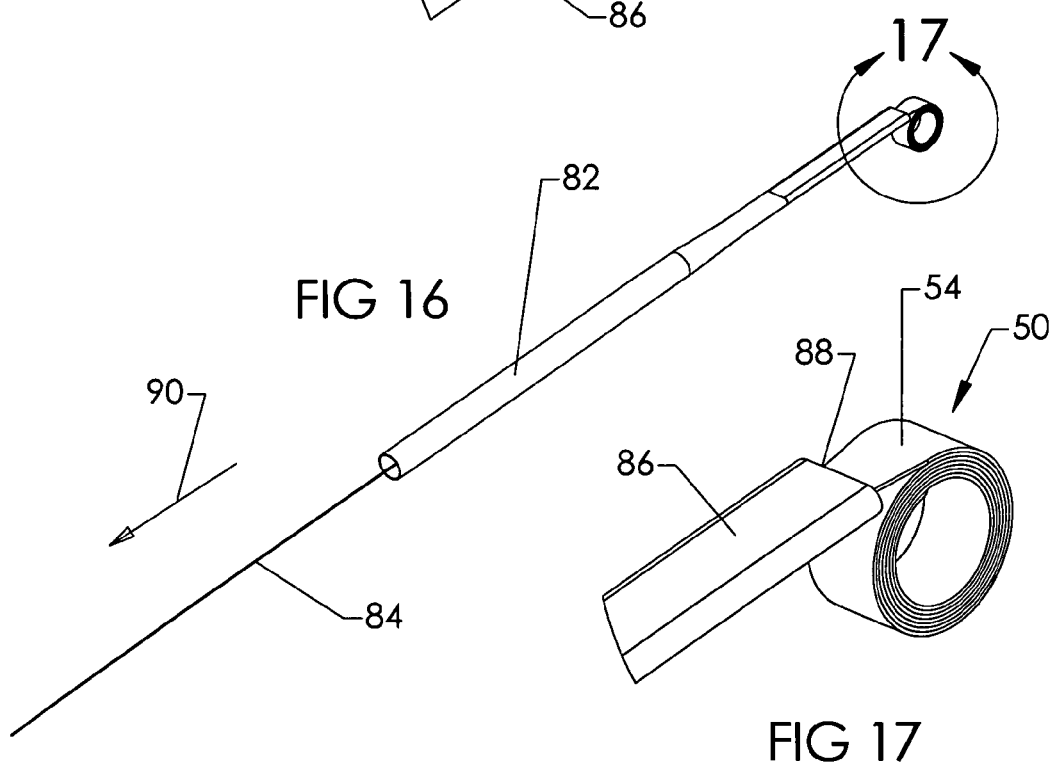

ELUTING COILS AND METHODS OF DEPLOYING AND RETRIEVING

CROSS REFERENCE TO RELATED APPLICATIONS

This application claims priority under 35 U.S.C. section 119(e) from U.S. Provisional Application Ser. No. 60/642,892, titled "Eluting Coils and Methods of Deploying and Retrieving", filed Jan. 10, 2005, by John L. Wardle, which is incorporated by reference herein in its entirety. This application is also related to U.S. patent application Ser. No. 10/386,260, filed Mar. 10, 2003, by John L. Wardle, titled "Surgical Coils and Methods of Deploying" which is also incorporated by reference herein in its entirety.

BACKGROUND

Systemic drug delivery is often ill-suited to the treatment of conditions occurring at one or more discrete sites within a patient's body, because it involves the delivery of the medication to sites other than the target site. Systemic agent delivery also requires the infusion of large doses of the medication to assure the delivery of a therapeutic dose to the target site, thereby creating the possibility of deleterious effects. Another problem of systemic administration is the inevitable fluctuations of drug concentrations that it produces. The dosage that can be delivered to the target site may be limited by the need to minimize unwanted effects in other parts of a patient's body. Furthermore, systemic delivery exposes the medication to possible degradation and elimination by the action of other bodily organs.

Conventional methods of drug therapy, as discussed above, often result in blood levels of the cytotoxic agent that are dangerous for the patient. Even with local administration of these agents, one must consider that blood flow of vessels as well as other transport mechanisms may dilute the local concentration of the therapeutic agent by a wash-out effect. The need remains, therefore, for systems and methods for localized delivery of therapeutic agents, including toxic therapeutic agents, which may be concentrated and localized intramurally within the affected tissue or vessel.

There is general need in many branches of medicine for improved localized internal delivery of substances including therapeutic agents and drugs and diagnostic agents into the walls of ducts, organs and vessels. In particular, there is need for effective systems and methods of delivery into tissue and into cells themselves within organs, ducts, tracts and vessels of the body via percutaneous and luminal access. Problems remain however in the exact method by which the local administration of drugs or therapeutic agents can be achieved. The problem is further complicated where it is desirable to deliver drug in relatively small amounts and the delivery device must be sufficiently small, biocompatible, impermeable and drug non-reactive. There is also a need in some circumstances for retrieval systems and methods of delivery devices which may be implemented at the conclusion of treatment embodiments or portions thereof.

SUMMARY

Some embodiments include eluting coils that can accurately dispense and distribute fluids and or dissolvable substances in site specific locations of a patient's body. Some embodiments of eluting coils may be configured to be subsequently retrieved from a delivery site.

Some embodiments include an eluting coil, having an elongate element with a longitudinal axis formed into a coiled enclosed configuration with an overlapped portion. Sections of the elongate element make contact with adjacent sections of the elongate element in the overlapped portion. The overlapped portion has a circumferential overlap of at least 300 degrees and has a pre-stressed configuration to ensure surface contact between overlapped portions of the elongate element. Some of these embodiments include a pre-stress of the pre-stressed configuration which is substantially constant around the coil. Some of these embodiments include a surface of the elongate element that has at least one reservoir with a channel. Some of these embodiments include stand-off members on at least a portion of the surface of the elongate element that are configured to produce a controlled eluting gap between coils segments when the elongate element is in a coiled configuration. Some of these embodiments include an elongate element having an interlocking configuration that may include a longitudinal groove in a first surface of the elongate element and a longitudinal ridge, configured to mate with the longitudinal groove on a second surface opposite the first surface. The interlocking configuration may be configured to create an eluting gap between adjacent coils of overlapped portions the elongate element in a coiled configuration. Some of these embodiments may include a tail member for removal after deployment.

Some embodiments of eluting coils for deployment within a body of a patient include a resilient elongate element having an inside surface, an outside surface, a pre-stressed non-coiled configuration in a restrained state and a coiled configuration in a relaxed state with the outside surface disposed adjacent the inside surface in an overlapped portion thereof. At least one dissolvable agent reservoir is disposed on the elongate element. In addition, at least one conduit having a pre-determined cross section is disposed in fluid communication between the dissolvable agent reservoir and an outside portion of the coiled configuration of the resilient elongate element in the relaxed state. Some of these embodiments include a resilient elongate element with a pre-stress of a substantially constant radius of curvature along a length of the resilient elongate element. Some of these embodiments include at least one stand-off member on a surface of the resilient elongate element and the at least one conduit comprises a controlled gap formed by the stand-off member between the inside surface and outside surface of the resilient elongate element in overlapped portions of the coiled configuration in the relaxed state. Some of these embodiments include a conduit formed from at least one channel disposed on a surface of the resilient elongate element.

Some embodiments of a method of deploying an eluting coil include providing an eluting coil for deployment within a body of a patient. The eluting coil includes a resilient elongate element having an inside surface, an outside surface, a pre-stressed non-coiled configuration in a restrained state and a coiled configuration in a relaxed state with the outside surface disposed adjacent the inside surface in an overlapped portion thereof. At least one dissolvable agent reservoir is disposed on the elongate element. At least one conduit having a pre-determined cross section is disposed in fluid communication between the dissolvable agent reservoir and an outside portion of the coiled configuration of the resilient elongate element in the relaxed state. The resilient elongate element of the eluting coil is disposed in a restrained state. A distal end of an elongate delivery member is disposed adjacent a target site within a patient's body and the resilient elongate element is moved along the elongate delivery member. The resilient elongate element is deployed from a distal end of the elongate delivery member and allowed to achieve a relaxed coiled configuration.

Some embodiments of a method of retrieving an eluting coil include providing an eluting coil deployed within a body of a patient in a relaxed coiled configuration. The eluting coil includes a resilient elongate element having an inside surface, an outside surface, a pre-stressed non-coiled configuration in a restrained state and a coiled configuration in a relaxed state with the outside surface disposed adjacent the inside surface in an overlapped portion thereof. At least one dissolvable agent reservoir is disposed on the elongate element. At least one conduit having a pre-determined cross section is disposed in fluid communication between the dissolvable agent reservoir and an outside portion of the coiled configuration of the resilient elongate element in the relaxed state. A tail member is disposed at an end of the resilient elongate element configured to facilitate removal of the eluting coil after deployment thereof. A retrieval device is advanced into the patient's body until a distal end of the retrieval device is disposed adjacent the eluting coil. A retraction element of the retrieval device is coupled to the tail member and the resilient elongate element is withdrawn into the retrieval device.

These features of embodiments will become more apparent from the following detailed description when taken in conjunction with the accompanying exemplary drawings.

BRIEF DESCRIPTION OF THE DRAWINGS

FIG. 3 shows a perspective view of an eluting coil similar to that of FIGS. 1 and 2 in a straightened configuration.

FIG. 4 is an enlarged view, in perspective, of the encircled portion 4 of FIG. 3 showing surface reservoirs and channels.

FIG. 9 shows a perspective view of an alternative embodiment of an eluting coil with an integrated retrieval tail.

FIG. 10 is an enlarged view, in perspective, of the encircled portion 10 of FIG. 9 showing a retrieval hole.

FIG. 11 shows a perspective view of an alternative embodiment of an eluting coil with an attached retrieval tail.

FIG. 12 is an enlarged view, in perspective, of the encircled portion 12 of FIG. 11 showing a retrieval loop.

FIG. 13 is an enlarged view, in perspective, of the encircled portion 13 of FIG. 11 showing a retrieval loop attachment.

FIG. 14 is a perspective view of a retrieval device including a retrieval cannula and a retraction element in the form of a retrieval wire disposed within the retrieval cannula, with a distal end of the retrieval cannula disposed adjacent an eluting coil and a distal end of the retrieval wire coupled to a tail extension of a resilient elongate element of the eluting coil to retrieve the eluting coil.

FIG. 15 is an enlarged view, in perspective, of the encircled portion 15 of FIG. 14 showing retrieval wire placed in a retrieval hole of the resilient elongate element of the eluting coil.

FIG. 16 is a perspective view of the retrieval wire and retrieval cannula with the resilient elongate element of the eluting coil being withdrawn into a distal port at a distal end of the retrieval cannula.

FIG. 17 is an enlarged view, in perspective, of the encircled portion 17 of FIG. 16 showing the resilient elongate element of the eluting coil being withdrawn into the retrieval cannula.

DETAILED DESCRIPTION

Figure 1:
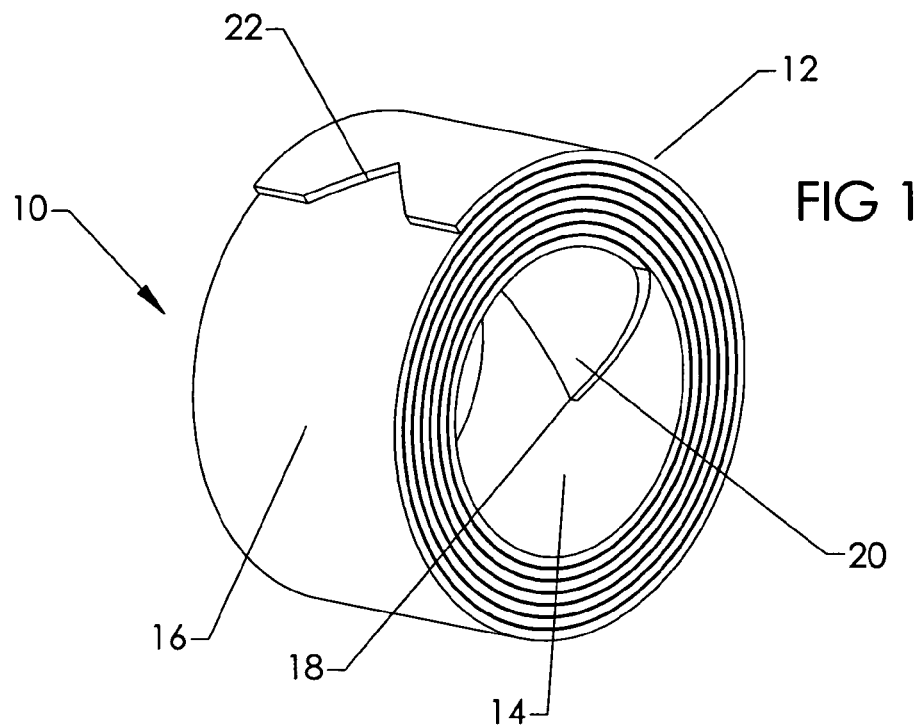
FIG. 1 illustrate a perspective view of an eluting coil having features of the disclosure.

FIGS. 1-4 illustrate an embodiment of an eluting coil 10 having a resilient elongate element 12 shown in a relaxed coiled configuration with approximately 7 revolutions. The resilient elongate element has an inside surface 14 and an outside surface 16 with the outside surface 16 in contact with the inside surface 14 in an overlapped portion over approximately 6 revolutions of circumferential overlap (about 2160 degrees). Some embodiments of eluting coils may have overlapped portions with an angular overlap of about 300 degrees to about 2160 degrees. The resilient elongate element 12 has a transverse cross section with a substantially flattened configuration producing a ribbon-like configuration for the resilient elongate element 12. The resilient elongate element also has a tissue penetrating point or tip 18 disposed at a distal end 20 of the resilient elongate element 12. The resilient elongate element 12 also has a wedge shaped recess 22 disposed at a proximal end 24 of the resilient elongate element 12. The relaxed coiled configuration of the eluting coil 10 includes a void or hole in the center thereof which may be disposed about target tissue of a patient upon deployment. Such tissue is mechanically captured by the deployed eluting coil 10 which may prevent movement or migration of the eluting coil 10 once it has been deployed.

The eluting coil 10 may be delivered to a target site in a patient's body (not shown) by methods disclosed in the incorporated application U.S. patent application Ser. No. 10/386, 260, filed Mar. 10, 2003, by John L. Wardle, titled "Surgical Coils and Methods of Deploying" ('260 Application). FIGS. 25-30 and the accompanying description of the '260 application describe embodiments of a delivery device having a delivery member or sheath that may be used to deploy the eluting coil 10 to a target site within a patient's body. Other embodiments of the '260 application may also be used.

Figure 2:
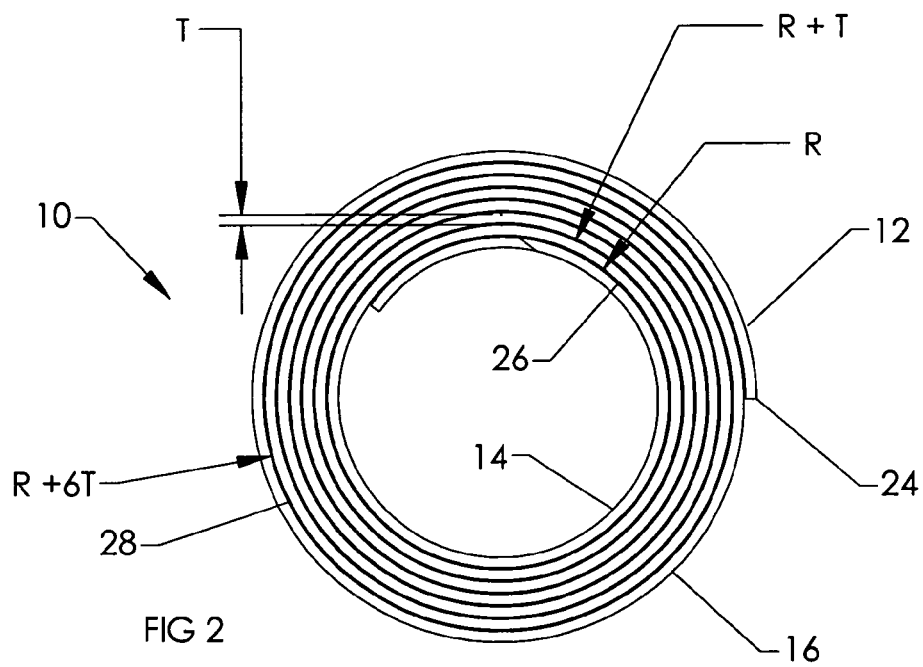
FIG. 2 is an elevational view of an eluting coil having features of the disclosure.

The resilient material of the resilient elongate element 12 is configured to resist deformation from the relaxed coiled configuration shown in FIGS. 1 and 2 and spring back to the relaxed coiled configuration when released from a restrained configuration, such as a straightened configuration, as shown in FIG. 3. The resilient elongate element 12 of eluting coil 10 and all eluting coil embodiments discussed herein may be made from a variety of materials including those that exhibit either great elasticity or shape memory properties. Suitable materials for fabrication include but are not limited to nickel titanium alloys (Nitinol), stainless steel, Elgiloy, MP35N or other high strength biocompatible materials. In addition to these materials eluting coils can be made from absorbable materials such as magnesium alloy which besides being absorbable has the added advantage that it does not interfere with magnetic resonance imaging (MRI).

FIG. 2 illustrates the geometry of some embodiments of eluting coils where a first surface of each circumferential overlap, or portion thereof, is in direct contact with a second surface of its neighboring overlap or portion of the resilient elongate element 12. Direct contact of the overlapping surfaces 14 and 16 ensures that there is no unintended free space between contacting surfaces 14 and 16. In some embodiments, the resilient elongate element 12 has a pre-stress with a constant curvature R along a length of the resilient elongate element 12. When the resilient elongate element 12 of the eluting coil 10 is ejected from a delivery device in a restrained non-coiled configuration, such as a straightened or substantially straightened configuration, the resilient elongate element will tend to spring back to the coiled configuration of the relaxed state of the resilient elongate element 12. In the relaxed coiled configuration, all layers of overlap tend to assume an unstressed state of constant radius of curvature R. As the resilient elongate element is deployed from a distal end of a delivery sheath or member, the distal end 20 begins to curl and assume a relaxed configuration. When the distal end 20 and the first revolution of the coil 10 enter a target site, the coil will be able to assume an unstressed state and assume a radial position R As subsequent layers of circumferential overlap are ejected from the delivery device the resilient elongate element 12 coils upon itself. The first overlap layer 26 will assume radius at rest of R+T and the sixth layer 28 will have a resulting radius of R+6T. The result is that as all layers are not allowed to assume the fully unstressed state of radius R. As such, compression forces, expansion forces or both cause the adjacent overlap layers of the resilient elongate element 12 to contact one another.

The surfaces 14 and 16 may be configured so as to provide a three dimensional drug eluting surface or reservoir, the modification could be as simple as a bead blast texture or more sophisticated techniques can be used as described in the following embodiments. FIGS. 3-4 illustrate an embodiment of resilient elongate element 12 of eluting coil 10 in a non-coiled restrained state with a straightened configuration. The elongate element 12 is shown with the distal end 20 extended opposite the proximal end 24. A plurality of axially consecutive longitudinal dissolvable agent reservoirs 30 and channels 32 are cut into the outside surface 16 elongate element 12. The reservoirs 30 and channels 32 are shown covering a substantial portion of outer surface 16, but any suitable portion of outer surface 16 or inner surface 14 could be used for such reservoirs 30 or channels 32. When the resilient elongate element 12 shown in FIGS. 3 and 4 is allowed to assume a relaxed coiled configuration, the reservoirs 30 and channels 32 cut into the outer surface 16 are pressed against the inner surface 14 such that the reservoirs 30 are sealed from an outside portion of the eluting coil 10 and a top portion of the channels are sealed to form a conduit in fluid communication between the respective reservoirs 30 and outside portion of the eluting coil 10. As shown in more detail in FIG. 4, the channels 32 may extend across a plurality of reservoirs 30 to a lateral edge 34 of the resilient elongate element 12. For some embodiments of eluting coils 10, some of the reservoirs or dissolvable agent depots 30 may be exposed when the resilient elongate element 12 of the eluting coil 10 is in a coiled configuration in a relaxed state. The exposure of such reservoirs 30 allows for initial delivery of a high dose of agent over a short period upon initial deployment of the eluting coil 10. The non-exposed or encapsulated reservoirs 30 will deliver agent from a dissolvable matrix over a course of time determined by the transverse cross section of the channels or conduits 32 and capacity of reservoirs 30.

Eluting coils 10 may be configured to be delivered to a target site in a patient's body with a wide range of agents, such as bioactive agents including drugs, antibiotic agents, growth factors, anti-inflammatory agents and the like disposed in a dissolvable matrix within reservoirs 30, channels 32 or both. Dissolvable matrix components may include, but are not limited to, lipid materials, gelatins and the like. FIG. 4 shows a dissolvable agent reservoir 30 with a dissolvable agent 36 disposed therein. Generally, some or all of the reservoirs 30 may have some dissolvable agent 36 disposed within them prior to deployment of the eluting coil 10. When the resilient elongate element 12 of the eluting coil 10 is ejected from the delivery device the overlapping surfaces will encapsulate and contain the reservoirs 30 and channels 32 as discussed above. Thereafter, the dissolvable agent will come in contact with body fluids via the conduits formed by the channels and the dissolvable agent will be delivered from the reservoirs 30 to a region outside the eluting coil 10 through the conduits formed by the encapsulated channels 32.

Reservoirs 30 may be formed into one surface 14 or 16 of the resilient elongate element 12, or may extend completely through the resilient elongate element 12. Channels 32 may be cut to a specific depth and width in order to provide a path or conduit for controlled release of the dissolvable agent 36, such as a bioactive agent, from the connected reservoir(s) 30 to tissue of a target site. The channels 32 may also contain the dissolvable agent 36. This embodiment of the eluting coil 10 provides a means for a broad spectrum of release profiles to be tailored to the requirements of a particular bioactive agent and may also be used to enable the delivery of multiple compounds simultaneously. For example, different zones of the surfaces 14 or 16 of the resilient elongate element 12 may be loaded with different agents, such as drugs or other biologically active agents. For example, some embodiments may include anti-inflammatory agents and therapeutic agents on a single eluting coil 10. For such embodiments, different agents may be separated into different reservoirs 30, or may be combined together into the same reservoir or reservoirs 30.

In addition, different zones or portions of the resilient elongate element 12 of the eluting coil 10 may be configured with varying reservoir 30 and channel 32 profiles. Different surfaces 14 and 16, including reservoirs 30 or channels 32 thereof, of the resilient elongate element 12 of the eluting coil 12 may also be loaded with different agents disposed within a dissolvable agent matrix. Also, two or more components of a multi-component drug or other agent that need to be combined in order to react or otherwise be activated may be placed on opposite surfaces 14 and 16 of the resilient elongate element 12 of the eluting coil 10. In such a configuration, the two or more components will then be combined or otherwise communicated with each other and activated when the eluting coil 10 is deployed and the opposing surfaces 14 and 16 make contact.

Figure 5:
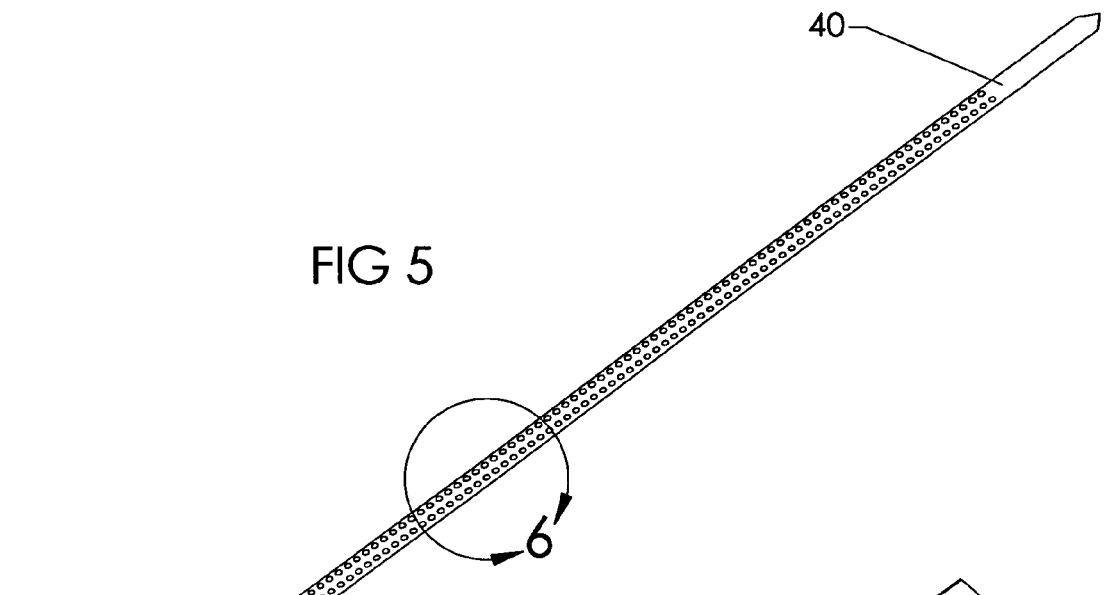
FIG. 5 illustrates a perspective view of an alternative embodiment of an eluting coil in a straightened configuration.
Figure 6:
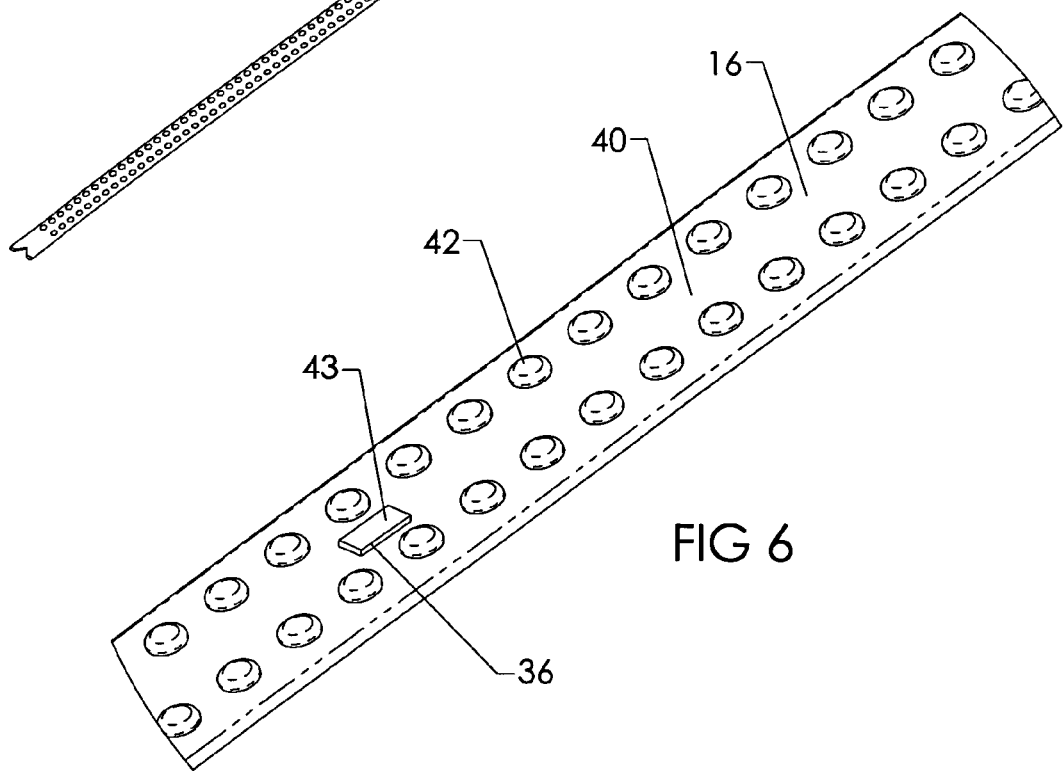
FIG. 6 is an enlarged view, in perspective, of the encircled portion 6 of FIG. 5 showing surface protrusions on the elongate member.

FIGS. 5-6 illustrate another embodiment of a resilient elongate element 40 of an eluting coil 10 in a restrained straightened state with some features that are common with the previous resilient elongate element embodiment 12. The resilient elongate element 40 has a series of surface protrusions or stand-off members 42 that are configured to create a space between overlapping surfaces 14 and 16 of the eluting coil 10 when deployed. The controllable gap or conduit created as a result of the stand-off members 42 will be substantially equal to the height of the stand-off members 42 when the resilient elongate element 40 is disposed in a coiled relaxed configuration. Inside surface 14 or outside surface 16 of the resilient elongate element 40 of the eluting coil 10 may be coated with a bioactive agent in a dissolvable matrix 36. A bioactive agent disposed in a dissolvable matrix 36 may also be disposed on inner portions of the resilient elongate element 40 between stand-off members in a dissolvable agent depot or reservoir 43, as shown in FIG. 6. For such an embodiment, a space or gap (such as the gap indicated by arrows 49 in the embodiment shown in FIG. 8 below) created by the stand-off members 42 between adjacent surfaces 14 and 16 of the resilient elongate element 40 in a relaxed coiled state or configuration will provide a controlled leak path or conduit for the bioactive agent in the dissolvable matrix 36 to reach an outside portion of the resilient elongate element 40 when in a relaxed coiled configuration.

Figure 7:
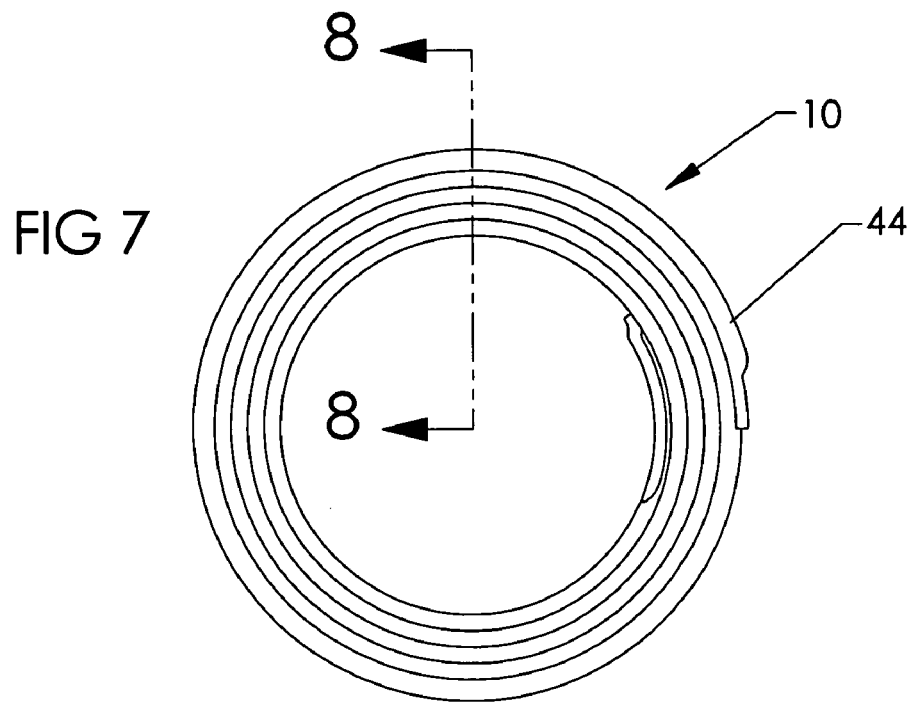
FIG. 7 is an elevational view of an eluting coil having an embodiment of a self-aligning coil configuration.
Figure 8:
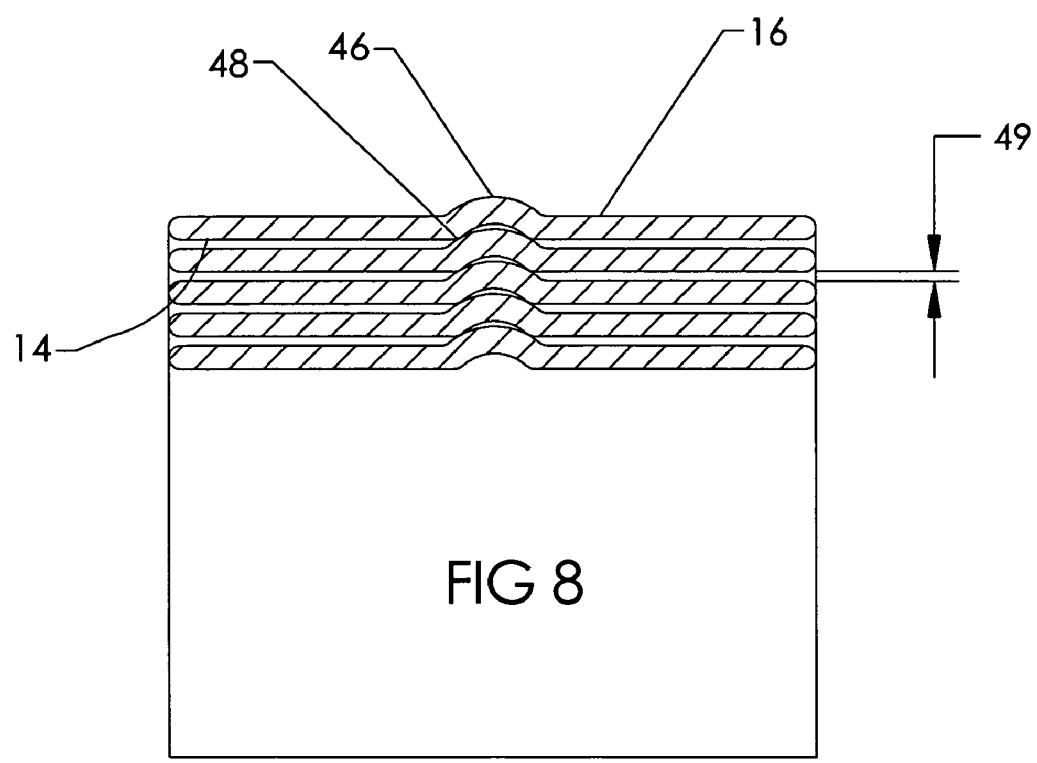
FIG. 8 is a transverse cross sectional view of the eluting coil of FIG. 7 taken along lines 8-8 of FIG. 7 illustrating an interlocking groove, raised ridge and eluting channel on the elongate element of the eluting coil.

FIGS. 7-8 illustrate an embodiment of eluting coil 10 which has a resilient elongate element 44 that is configured as an interlocking eluting coil 10 when deployed. FIG. 8 shows a transverse cross sectional view of the eluting coil 10 which shows a raised longitudinal ridge 46 disposed on an outer or first surface 16 of the resilient elongate element 44. The longitudinal ridge 46 is configured to mate and interlock with a longitudinal groove 48 extending longitudinally along a second or inner surface 14 of the elongate element. An interlocking engagement between the raised longitudinal ridge 46 and longitudinal groove 48 is configured such that the engagement prevents the remainder of the overlap surfaces 14 and 16 from contacting. For such a configuration, a controllable gap or space indicated by arrows 49 is created. The controllable gap between adjacent sections of the resilient elongate element 44 functions as a conduit between an inner portion of the eluting coil 10 and an outside portion of the eluting coil 10 when the coil is in a coiled relaxed state.

Reservoirs, such as reservoirs 30 discussed above may be disposed on one or both of the surfaces 14 and 16 of the resilient elongate element 44 with the controllable gap providing a conduit between the reservoirs and an outside portion of the coil 10. Also, one or more surfaces 14 and 16 of the resilient elongate element 44 may be coated with the bioactive agent in a dissolvable matrix with the space or gap between surfaces of the resilient elongate element 44 providing a controlled leak path or conduit for the bioactive agent to an outside portion of the eluting coil 10 in a coiled relaxed state. Although the embodiment shown in FIGS. 7 and 8 includes one raised longitudinal ridge 46 and one longitudinal groove 48 on an opposite surface of the resilient elongate element 44, the resilient elongate element 44 may include multiple raised longitudinal ridge elements and mating longitudinal grooves.

FIGS. 9-13 illustrate alternate embodiments of eluting coils which can be removed from the treatment site after deployment if necessary. These eluting coil embodiments include an extension tail that is configured to be coupled to by a device that may then be used to apply a retractive force upon the deployed eluting coil. The extension tail may be an integral part of the resilient elongate element of the eluting coil itself or be a separate attached feature or element.

FIGS. 9 and 10 illustrate an eluting coil 50 that may have features, dimensions and materials similar to or the same as those of the eluting coil 10 discussed above. Eluting coil 50 also includes a tail extension 52 formed integrally with a proximal end 54 of a resilient elongate element 56 of the eluting coil 50. The tail extension includes a hole 58 disposed at a proximal end 60 of the tail extension 52 in order to facilitate capture and retrieval of the eluting coil 50 after deployment thereof. The proximal end 60 of the tail extension may include radiopaque material or otherwise be configured to be radiopaque in order to facilitate visualization of the hole 58 of the tail extension 52 under X-ray or fluoroscopy during a retrieval procedure. The tail extension embodiment 52 shown in FIGS. 9 and 10 has a substantially straight configuration in a relaxed state in order to extend away from the eluting coil 50 and facilitate location and coupling of the tail extension 52. In use, the proximal end 60 of the tail extension 52 may be placed just under the surface of the skin of a patient in order to avoid infection and make the tail extension 52 easy to relocate or access. However, under some circumstances, such as where only short term implantation is necessary, the tail extension 52, the proximal end 60 of the tail extension 52 or both may be deployed so as to breach through the surface of the skin of the patient.

FIGS. 11-13 illustrate an eluting coil 62 that may have features, dimensions and materials similar to or the same as those of the eluting coil 10 discussed above. Eluting coil 62 also includes a tail extension 64 that is a separate element from the resilient elongate element 66 of the eluting coil 62. The tail extension 64 includes a loop of a flexible element, such as suture material, that extends through a hole 68 in a proximal end 70 of the resilient elongate element 66. The tail extension includes a loop 72 disposed at a proximal end of the tail extension 64 in order to facilitate coupling to the tail extension 64 and capture and retrieval of the eluting coil 62 after deployment thereof. The loop 72 of the tail extension 64 may include radiopaque material or otherwise be configured to be radiopaque in order to facilitate visualization of the loop 72 of the tail extension 64 under X-ray or fluoroscopy during a retrieval procedure. Just as with eluting coil embodiment 50 discussed above, the proximal end of the tail extension 64 may be placed just under the surface of the skin of a patient in order to avoid infection and make the tail extension 64 easy to relocate or access. However, under some circumstances, such as where only short term implantation is necessary, the tail extension 64, the proximal end of the tail extension 64 or both may be deployed so as to breach through the surface of the skin of the patient.

FIGS. 14-17 illustrate a removal or retrieval method and device that may be employed to remove an eluting coil 50 after deployment, and in particular, after deployment within tissue of the body of a patient. FIGS. 14 and 15 show a perspective view of a retrieval device 80 coupled to eluting coil 50. The retrieval device 80 includes a retrieval cannula 82 and a retraction element in the form of a retrieval wire 84 disposed within the retrieval cannula 82. A distal end 86 of the retrieval cannula 82 is disposed adjacent eluting coil 50. A hooked distal end 88 of the retrieval wire 84 is disposed through or otherwise coupled to hole 58 the tail extension 52 of the resilient elongate element 54 of the eluting coil 50 to retrieve the eluting coil 50. The retrieval cannula is configured as an elongate hollow member that may be made from a high strength material such as stainless steel or the like. A distal section 87 of the retrieval cannula 82 may have an optional flattened or oblong transverse cross section in order to better accommodate the flattened transverse cross section or ribbon-like configuration of some resilient elongate element embodiments. In addition, the flattened or oblong transverse cross section may also be useful for tissue penetration during deployment or positioning within tissue of a patient while minimizing trauma to the tissue surrounding the retrieval cannula 82 during tissue penetration.

In some embodiments of methods of retrieval of a deployed eluting coil 50, the retrieval process begins with identifying or locating the proximal end 60 of the tail extension 52. Once located, the hooked distal end 88 of a retrieval wire 84 it placed through the hole 58 (or a loop 72 of an embodiment of an eluting coil 62 as shown in FIGS. 11-13) as shown in FIG. 15. The proximal end of the retrieval wire 84 is the back loaded or withdrawn into the cannula 82. The proximal end of the retrieval wire 84 may held stationary while the distal end 86 of the cannula 82 is advanced distally until the distal end 86 contacts the resilient elongate element 54 of the eluting coil 50. The cannula 82 may then be held stationary and the retrieval wire 84 is pulled or withdrawn proximally, as indicated by arrow 90, shown in FIG. 16, which in turn pulls the resilient elongate element 54 of the eluting coil 50 into the cannula 82 and uncoils the eluting coil 50 and imparts a restrained non-coiled configuration on the resilient elongate element 54 as the resilient elongate element 54 is withdrawn into the cannula 82.

FIGS. 16 and 17 show a perspective view of the retrieval wire 84 and retrieval cannula 82 with the resilient elongate element 54 of the eluting coil 50 being withdrawn into a distal port 88 disposed at the distal end 86 of the retrieval cannula 82. The retrieval wire 84 and resilient elongate element 54 are being withdrawn into the retrieval cannula along a direction indicated by arrow 90.

Figure 18:
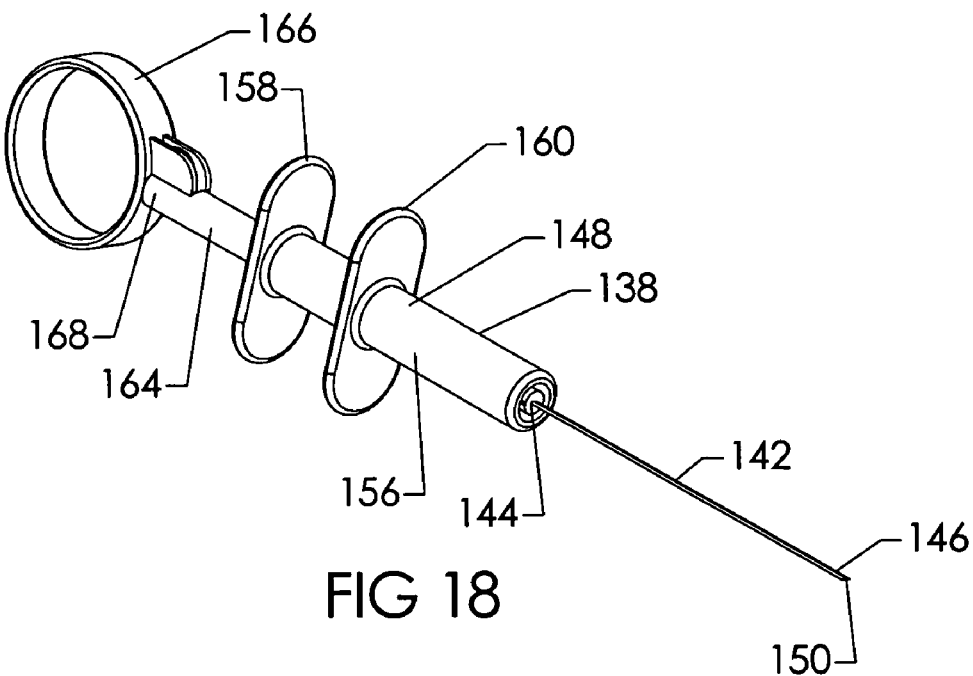
FIG. 18 is a perspective view of a ratcheting delivery device configured to deliver and deploy eluting coils, with a thumb ring of the delivery device in a proximal retracted position.

FIGS. 18-23 illustrate an embodiment of a delivery device 138 and methods of using the delivery device 138 for deployment of eluting coils 140. FIG. 18 is a perspective view of an embodiment of a delivery device 138 having an elongate delivery sheath 142 with a proximal end 144 a distal end and a delivery actuator 148 secured to the proximal end 144 of the delivery sheath 142. The delivery sheath 142 is an elongate hollow tube having a sharpened distal tip 150 shown in FIG. 20. The delivery sheath 142 has an interior lumen 152 which is configured to constrain a resilient elongate element 154 of an eluting coil 140 and allow the constrained resilient elongate element 154 to be advanced through the lumen 152 of the delivery sheath 142 to a deployment site. The eluting coil 140 and resilient elongate element 154 may have features, dimensions and materials which are similar to or the same as those of any of the eluting coil or resilient elongate element embodiments discussed herein. For the configuration shown, the delivery sheath 142 can be made from any suitable high strength metal, composite or polymer.

Suitable metals for construction of the delivery sheath 142 may include stainless steel, Nitinol, MP35N and the like. The delivery actuator 148 has an elongate cylindrically shaped body portion 156 with a proximal flange 158 and a distal flange 160. The body portion 156 has an internal bore 162 that is sized to accept a cylindrical actuator 164 in sliding relation to the body portion 156. A thumb ring 166 is disposed at a proximal end 168 of the cylindrical actuator 164 to facilitate the grip of an operator of the delivery device 138. The body portion 156 and cylindrical actuator 164 can be made from a variety of suitable medical grade materials, including metals, composites and polymers. Specifically, polymers such as ABS plastic, PVC, polycarbonate and the like may be used.

Figure 21:
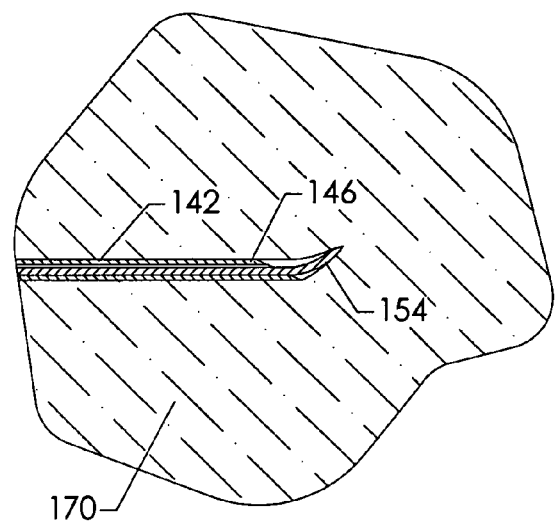
FIG. 21 illustrates a sharpened distal tip of an eluting coil penetrating tissue during deployment.
Figure 22:
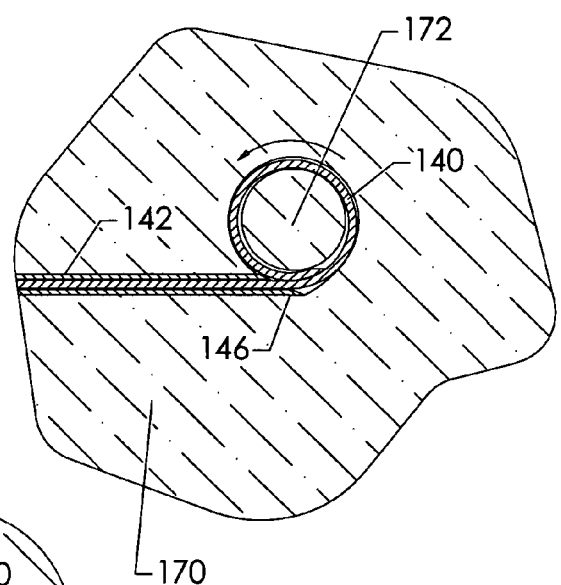
FIG. 22 illustrates a schematic view of the eluting coil of FIG. 21 in a further deployed configuration, the direction of deployment being indicated by the arrow.
Figure 23:
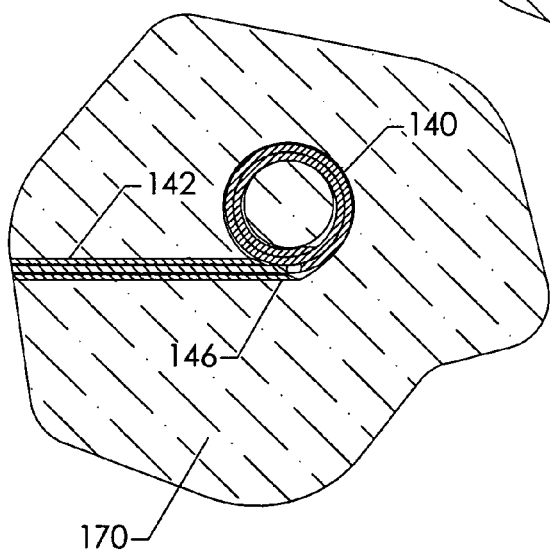
FIG. 23 illustrates a schematic view of the eluting coil in a completely deployed state within tissue.

An eluting coil 140 being deployed from a distal end 146 of the delivery sheath 142 into tissue 170 of a target tissue site is shown in FIGS. 21-23. The resilient elongate element 154 of eluting coil 140 may include the pre-stressed self-forming embodiment shown, wherein the resilient elongate element 154 returns to a relaxed coiled configuration, that is the configuration in a relaxed state, as the resilient elongate element 154 exits the distal end 146 of the delivery sheath 142 and the constraint of the delivery sheath 142 is removed. The eluting coil 140 is shown mechanically capturing a portion of tissue 172 of the target tissue site as it encircles the tissue.

Embodiments of delivery device 138 shown in FIG. 18 may use low profile delivery sheaths in the form of hollow needles with sharpened distal ends to deliver eluting coils to a target tissue site. The delivery sheath 142 is a straight tube with a distal tissue penetrating point 150 and is stiffer than an eluting coil 140 to be delivered therethrough. The geometry of the distal point of the delivery sheath 142 can be important in some embodiments. The distal point 150 needs to easily penetrate tissue while also providing clearance for the surgical coil 140 as it is being delivered without substantial restriction to assume the relaxed geometry of the surgical coil 140. For some delivery sheath 142 embodiments, the distal point can have an angle of about 25 degrees.

Delivery sheath 142 may have an internal profile that can slidably receive an elongate element 154 of an eluting coil 140 along their full length and will straighten them out into a restrained substantially straight configuration in doing so. Eluting coil 140 may be pre-loaded into the delivery sheath 142 prior to use. The maximum number of eluting coils 140 that a delivery sheath 142 can accommodate is limited by its length, however, some applications may require only a single eluting coil 140 be used. In a delivery device 138 having a multiple eluting coil 140 configuration, eluting coils 140 may be stacked end to end within the delivery sheath 142.

Figure 19:
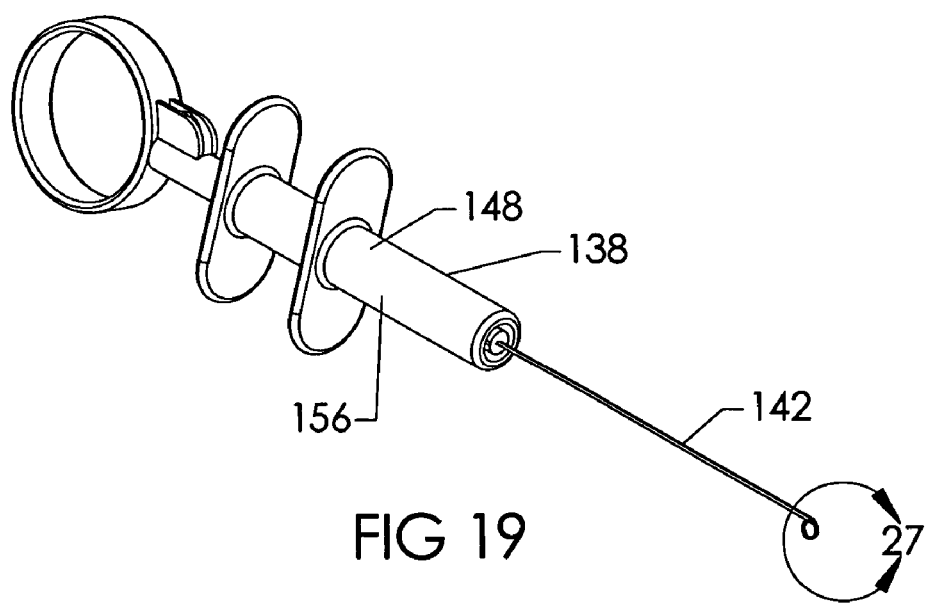
FIG. 19 is a perspective view of the delivery device of FIG. 18 with the thumb ring of the delivery device in an advanced distal position with an eluting coil being deployed from a distal end of a delivery sheath of the delivery device.
Figure 20:
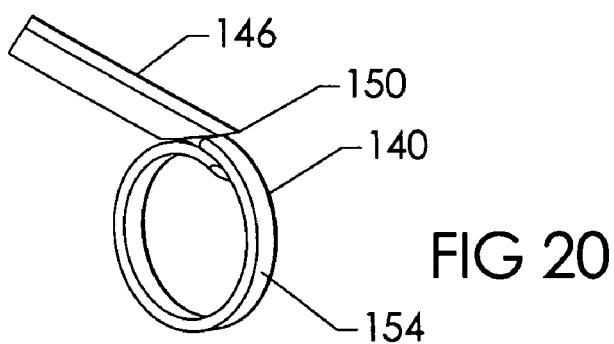
FIG. 20 is an enlarged view, in perspective, of the encircled portion 20 of FIG. 19 showing a distal section of the delivery device.

In one embodiment of use, the distal end 146 of the delivery sheath 142 is placed at a target site, a thumb ring 166 of the cylindrical actuator 164 is then moved distally as shown in FIG. 19 which pushes an advancing ribbon (not shown) which in turn pushes the most proximal eluting coil which then ejects the most distal eluting coil from the device 138 as shown in FIG. 20.

There are varieties of techniques that can be employed with these low profile delivery devices 138 to access target sites. The delivery sheath 142 can be used in the same manner as a hypodermic needle is for drug delivery (direct incision). Alternatively they can be placed within the working channel of an endoscope or cannula. All methods allow the physician to completely or partially implant a coil in tissue at an anterior or posterior location.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Alternate embodiments may include the combination of various features of different embodiments. For example, some or all of the features of the embodiments shown in FIG. 4 may be combined with some or all of the features of the embodiments shown in FIG. 8. Accordingly, it is not intended that the invention be limited by the forgoing detailed description.

What is claimed is:

1. An eluting coil for deployment within a body of a patient, comprising:
    a resilient elongate element including a flattened ribbon-like configuration, a first surface, a second surface, a pre-stressed non-coiled configuration in a restrained state that ensures contact between the first surface and the second surface in adjacent sections of the elongate element when the elongate element is in a coiled configuration in a relaxed state with the first surface disposed adjacent the second surface in an overlapped portion of the elongate element;

at least one dissolvable agent reservoir disposed on the elongate element in a position that is contained from an outside portion of the eluting coil when the elongate element is in a relaxed coiled configuration; and structure on the first surface configured to form at least one conduit between the first and second surfaces of adjacent sections of the elongate element in the coiled configuration, the at least one conduit including a pre-determined cross section and being in fluid communication between the contained dissolvable agent reservoir and an outside portion of the coiled configuration of the resilient elongate element in the relaxed state.

2. The eluting coil of claim 1 wherein the pre-stress of the pre-stressed non-coiled configuration of the resilient elongate element comprises a substantially constant radius of curvature along a length of the resilient elongate element sufficient to generate forces that ensure contact between adjacent sections of the elongate element when in the coiled configuration.

3. The eluting coil of claim 1 wherein the structure on the first surface of the resilient elongate element which is configured to form at least one conduit comprises at least one stand-off member on the first surface and the at least one conduit comprises a controlled gap formed by the stand-off member between the first surface and second surface of the resilient elongate element in overlapped portions of the coiled configuration in the relaxed state.

4. The eluting coil of claim 1 wherein the structure on the first surface of the resilient elongate element which is configured to form at least one conduit comprises at least one stand-off member on the first surface and the at least one dissolvable agent reservoir comprises a depot adjacent the stand-off member on an inner portion of the resilient elongate element in a controlled gap between the first surface and second surface of the resilient elongate element in overlapped portions of the coiled configuration in the relaxed state.

5. The eluting coil of claim 3 wherein the stand-off member comprises a longitudinal ridge disposed on the first surface of the resilient elongate element.

6. The eluting coil of claim 5 further comprising a longitudinal groove disposed on a second surface of the elongate element configured to mate with the longitudinal ridge on the first surface and whereby the coiled configuration of the elongate element comprises an interlocking configuration.

7. The eluting coil of claim 1 wherein the structure on the first surface of the resilient elongate element which is configured to form at least one conduit comprises at least one channel disposed on the first surface of the resilient elongate element.

8. The eluting coil of claim 7 wherein the at least one channel extends to a lateral edge of the resilient elongate element.

9. The eluting coil of claim 1 wherein the overlapped portion comprises a circumferential overlap of the resilient elongate element of at least about 300 degrees.

10. The eluting coil of claim 1 further comprising a dissolvable agent disposed within the at least one dissolvable agent reservoir.

11. The eluting coil of claim 10 wherein the dissolvable agent comprises a therapeutic agent.

12. The eluting coil of claim 1 wherein the coiled configuration of the relaxed state is substantially circular.

13. The eluting coil of claim 1 wherein the coiled configuration comprises an outer transverse dimension of less than about 1 cm.

14. The eluting coil of claim 1 wherein the resilient elongate element further comprises a tail extension disposed at an end of the resilient elongate element and configured to facilitate coupling thereto and removal of the eluting coil after deployment.

15. The eluting coil of claim 1 wherein the resilient elongate element further comprises a sharpened end configured to penetrate tissue upon axial advancement of the resilient elongate element during deployment of the eluting coil.

16. A method of deploying an eluting coil, comprising:
providing an eluting coil for deployment within a body of a patient, including:
a resilient elongate element including a flattened ribbon-like configuration, a first surface, a second surface, a pre-stressed non-coiled configuration in a restrained state that ensures contact between the first surface and second surface in adjacent sections of the elongate element when the elongate element in a coiled configuration in a relaxed state with the first surface disposed adjacent the second surface in an overlapped portion of the elongate element;
at least one dissolvable agent reservoir disposed on the elongate element in a position that is contained from an outside portion of the eluting coil when the elongate element is in a relaxed coiled configuration; and
structure on the first surface configured to form at least one conduit between inside the first and second surfaces of adjacent sections of the elongate element in a coiled configuration, the at least one conduit including a pre-determined cross section and being in fluid communication between the contained dissolvable agent reservoir and an outside portion of the coiled configuration of the resilient elongate element in the relaxed state;
disposing the resilient elongate element of the eluting coil in a restrained state;
disposing a distal end of an elongate delivery member adjacent a target site within a patient's body;
moving the resilient elongate element along the elongate delivery member and deploying the resilient elongate element from a distal end of the elongate delivery member; and
allowing the resilient elongate element of the eluting coil to achieve a relaxed coiled configuration and form the at least one conduit and contain the at least one agent reservoir between the first surface and second surface of adjacent sections of the elongate element.

17. A method of retrieving an eluting coil, comprising:
providing an eluting coil deployed within a body of a patient in a relaxed coiled configuration, the eluting coil including:
a resilient elongate element including a flattened ribbon-like configuration, a first surface, a second surface, a pre-stressed non-coiled configuration in a restrained state that ensures contact between the first surface and the second surface in adjacent sections of the elongate element when the elongate element is in a coiled configuration in a relaxed state with the first surface disposed adjacent the second surface in an overlapped portion of the elongate element,
at least one dissolvable agent reservoir disposed on the elongate element in a position that is contained from an outside portion of the eluting coil when the elongate element is in a relaxed coiled configuration, structure on the first surface configured to form at least one conduit between first and second outside surfaces of adjacent sections of the elongate element in a coiled configuration, the at least one conduit including a pre-determined cross section and being in fluid communication between the contained dissolvable agent reservoir and an outside portion of the coiled configuration of the resilient elongate element in the relaxed state, and a tail member disposed at an end of the resilient elongate element configured to facilitate removal of the eluting coil after deployment thereof;

advancing a retrieval device into a patient's body until a distal end of the retrieval device is disposed adjacent the eluting coil;

coupling a retraction element of the retrieval device to the tail member; and withdrawing the resilient elongate element into the retrieval device.

18. The method of claim 16 wherein the structure on the first surface of the resilient elongate element which is configured to form at least one conduit comprises at least one stand-off member on the first surface and allowing the resilient elongate element of the eluting coil to achieve a relaxed coiled configuration and form the at least one conduit between the first surface and second surface of adjacent sections of the elongate element comprises forming a controlled eluting gap between adjacent sections of the elongate element with the at least one stand off member on the first surface of the elongate member.

19. The method of claim 16 wherein the structure on the first surface of the resilient elongate element which is configured to form at least one conduit comprises at least one channel disposed on the first surface and allowing the resilient elongate element of the eluting coil to achieve a relaxed coiled configuration and form the at least one conduit between the first surface and second surface of adjacent sections of the elongate element comprises containing the at least one channel disposed on the first surface of the elongate element with a surface of an adjacent section of the elongate element in a coiled configuration.

* * * * *

UNITED STATES PATENT AND TRADEMARK OFFICE
CERTIFICATE OF CORRECTION

PATENT NO. : 7,731,705 B2
APPLICATION NO. : 11/328884
DATED : June 8, 2010
INVENTOR(S) : John L. Wardle It is certified that error appears in the above-identified patent and that said Letters Patent is hereby corrected as shown below:

Claim 16, Column 12, Lines 30-31 should read:

"one conduit between the first and second surfaces of adjacent sections of the elongate element in a"

Signed and Sealed this

Fourteenth Day of December, 2010

David J. Kappos
*Director of the United States Patent and Trademark Office*